United States Patent [19]

Smigel

[11] Patent Number: 4,608,015

[45] Date of Patent: Aug. 26, 1986

[54] METHOD FOR SELECTING THE COLORATION OF A BONDING COMPOSITE FOR A DISCOLORED TOOTH

[76] Inventor: Irwin E. Smigel, 635 Madison Ave., New York, N.Y. 10022

[21] Appl. No.: 630,964

[22] Filed: Jul. 16, 1984

[51] Int. Cl.[4] .............................................. A61C 19/10
[52] U.S. Cl. ...................................... 433/26; 434/104; 434/98
[58] Field of Search ......................... 433/26, 217, 215; 434/98, 99, 101, 102, 104, 100

[56] References Cited

U.S. PATENT DOCUMENTS

| | | | |
|---|---|---|---|
| 1,582,122 | 4/1926 | Clapp | 433/26 |
| 1,709,975 | 4/1929 | Foshay | 434/98 |
| 1,842,923 | 1/1932 | Wannemacher | 433/26 |
| 2,240,053 | 4/1941 | Richardson | 434/98 |
| 2,462,606 | 2/1949 | Brodeur | 434/104 |
| 3,184,864 | 5/1965 | Johnson | 434/104 |
| 3,229,385 | 1/1966 | De Pauw | 434/98 |
| 3,507,042 | 4/1970 | Hana | 433/26 |
| 4,150,485 | 4/1979 | Lee, Jr. et al. | 433/217 |
| 4,241,520 | 12/1980 | Norton | 434/102 |

Primary Examiner—John J. Wilson
Attorney, Agent, or Firm—Roberts, Spiecens & Cohen

[57] ABSTRACT

A shade guide for dental use comprising a pair of superimposed discs rotatable with respect to one another, one disc being a lower disc with a plurality of regions of different colors representative of different tooth discolorations of the patient, the other disc being an upper disc with a plurality of transparent regions representative of coloration of composite material adapted for being bonded to teeth. By relatively rotating the discs, the transparent regions of the upper disc successively cover the regions of different colors of the lower disc to provide a resultant coloration which neutralizes the discolored tooth and most closely matches the final coloration of the tooth of the patient.

3 Claims, 1 Drawing Figure

U.S. Patent    Aug. 26, 1986    4,608,015
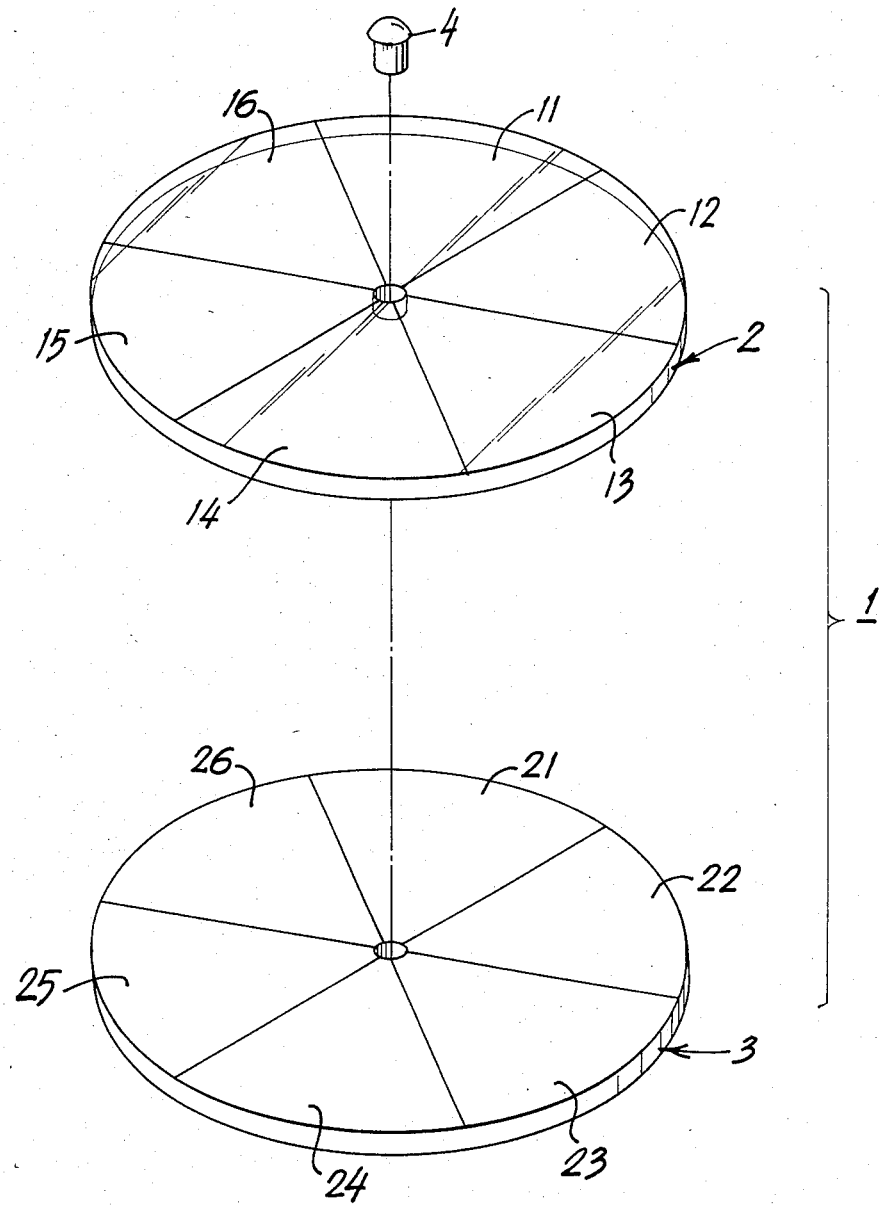

METHOD FOR SELECTING THE COLORATION OF A BONDING COMPOSITE FOR A DISCOLORED TOOTH

FIELD OF THE INVENTION

The invention is directed to an apparatus which will enable a dentist to select the coloration of a bonding composite in order to neutralize the discoloration of a tooth onto which the bonding composite is placed.

The invention further relates to a method for making the selection of the coloration of the bonding composite.

BACKGROUND

Current practice in dentistry includes the application of composite bonding materials onto teeth for various purposes such as reshaping and recoloring.

The composite material is generally composed of a resinous substance which is polymerized in situ and which provides a hard bearing surface which has the natural appearance of a normal tooth.

The development of composite restorations of tooth color represents one of the major advances in dentistry in the past twenty-five years and has revolutionized the profession from an aesthetic concept. The use of composite material in conjunction with the evolution of light activation with it's capability of controlling setting time and the dentist's ability to etch the enamel of the teeth and thus bond the composite material directly onto the tooth represents an important aspect of modern dentistry known as bonding. Bonding enables the dentist to close spaces between teeth, repair chips in teeth, cover discolorations and reshape abnormally shaped teeth.

There are three types of composite material:

A. The conventional material which is composed of 76% inorganic filler material, such as quartz or Barium glass and 24% Resin Matrix, such as BIS GMA which is the reactive product of BIS Phenol A and Glycidyl Methyl acrylic.

B. Microfill—composed of 35-55% inorganic filler—such as fumed silica and 45-65% Resin Matrix, generally BIS GMA.

C. Hybrid—composed of a "combination" inorganic filler such as both Barium glass and fumed silica as well as a resin matrix.

In using the composite material to cover discolored teeth, the dentist is constantly confronted with a choice of colorations for the bonding material which the dentist selects on the basis of visualization and expectation as to final coloration.

Sometimes a selection of bonding material is made which, when applied onto the discolored tooth and hardened in place, does not produce the desired final tooth coloration. This is because there are two variables consisting of the coloration of the bonding material and the coloration of the tooth and these are not brought into juxtaposition until the bonding material has been placed onto the tooth. The selection of the coloration of the composite material does not take into account the discoloration of the tooth onto which the bonding material is placed and frequently when the bonding material has been placed on the discolored tooth, a strange and undesired final color is obtained.

SUMMARY OF THE INVENTION

An object of the invention is to provide a shade guide for a dentist which will simplify and clarify the color selection for the composite material to be put on a discolored tooth.

A further object of the invention is to provide a shade guide which will enable the dentist to observe the resultant tooth color which will be obtained when the composite material is placed on the discolored tooth.

According to a particular object of the invention, a shade guide is provided which will enable the dentist to employ a coloration of bonding material which will effectively neutralize the discoloration of the tooth onto which it is applied.

Still another object of the invention is to provide a shade guide in which a plurality of regions representative of coloration of composite material can be successively superimposed on regions of different colors representative of different tooth discolorations of a patient.

Still another object of the invention is to provide a shade guide which is of simple construction and is easily utilized to enable a dentist to select the coloration of a composite material which will neutralize the discoloration of a discolored tooth.

In accordance with the above and further objects of the invention, there is provided a shade guide for dental use which comprises superposed discs rotatable with respect to one another, one disc being a lower disc with a plurality of regions of different colors representative of different tooth discolorations of a patient, the other disc being an upper disc with a plurality of transparent regions representative of coloration of composite material adapted for being bonded onto teeth. The transparent regions of the upper disc successively cover the regions of different colors of the lower disc upon relative rotation of the discs to provide a resultant coloration which can be matched to the desired final color shade of the tooth of the patient and thereby provide the coloration of the composite material necessary to neutralize the discolored tooth.

According to a preferred embodiment, the discs have a common axis of relative rotation and the regions on each disc are of triangular shape with an apex at said common axis.

In accordance with one embodiment of the invention, the number of regions on the discs are the same.

A further object of the invention is to provide a method for selecting the coloration of a bonding composite adapted for being applied to a discolored tooth to neutralize the discoloration of the tooth.

The method comprises selecting one of a plurality of different colorations which most closely matches the discoloration of a tooth to be bonded, superimposing on the selected coloration a plurality of transparent regions each of a coloration corresponding to composite material adapted for being bonded onto a tooth, and selecting one of said transparent regions which when superposed in said selected coloration corresponding to the discolored tooth most closely neutralizes said selected coloration.

BRIEF DESCRIPTION OF THE DRAWING

The sole FIGURE of the drawing is an exploded view of a shade guide according to a preferred embodiment of the invention.

DETAILED DESCRIPTION OF A PREFERRED EMBODIMENT

The invention will be described hereafter with reference to a preferred embodiment of a shade guide according to the invention with reference to the attached drawing wherein there is seen an exploded view of the shade guide 1 which comprises an upper disc 2 pivotably connected to a lower disc 3 by a rivet or similar attachment 4 which allows the disc 2 to be superimposed on the disc 3 and to be relatively rotatable thereabove. The discs 2 and 3 are circular and of the same extent so that when they are superimposed on one another, the thickness of the shade guide 1 will be equal to the combined thickness of discs 2 and 3.

The discs are approximately 0.35 to 0.5 mm in thickness. The discs are preferably made of a plastic material and the upper disc 2 is transparent whereas the lower disc 3 is opaque. The lower disc 3 could also be made of cardboard or suitable hard material other than plastic.

Each disc is provided with a plurality of separate distinct regions of which, on disc 2 the regions are designated by numerals 11-16, each region occupying a 60° sector of the disc. The lower disc is formed with six regions designated 21-26.

When discs 2 and 3 are superimposed on one another and rotated relative to one another, each of the transparent regions 11-16 can be successively superimposed on each of the regions 21-26 on the lower disc.

The regions 11-16 are of different colors representative of the coloration of composite material adapted for being bonded onto the teeth of a patient.

The regions 21-26 on the lower disc 3 are opaque regions each of a different color representative of different tooth discolorations of the patient.

When the discs 2 and 3 are relatively rotated with respect to one another, the transparent regions 11-16 successively cover the regions 21-26 of different colors of the lower disc and provide a resultant coloration which can be matched to the final desired color shade of the patient and thereby provide an effective neutralization of the discolored tooth.

This allows the dentist to select the coloration of the composite material which is to be applied to the discolored tooth of the patient in order to render the resulting tooth neutralized in color and adapted for receiving a final coating of bonding material to provide the desired finished coating for the tooth.

In operation, the dentist selects the coloration of a region 21-26 which most closely matches the discoloration of the tooth of the patient which is to be bonded.

The disc 2 is then successively rotated to superimpose the transparent regions 11-16 on the selected region 21-26 until the resultant coloration most closely neutralizes the coloration of the region 21-26.

When this has been achieved, the dentist is advised of the coloration of the bonding material which is to be applied to the discolored tooth in order to render the discolored tooth neutralized so that when the final coloration of the bonding material is applied to the now initialized tooth, the final coloration of the tooth will conform with that of the selected final coloration. In the absence of a neutralization step, the application of the final coloration onto the discolored tooth will produce a coloration which is not the same as that of the color of the finally applied bonding material.

The shade guide of the invention simplifies and clarifies the color selection for the dentist and permits the dentist to observe the intermediate tooth color and properly choose a final shade.

Although the invention has been described in relation to a specific embodiment, it will become apparent to those skilled in the art that numerous modifications and variations can be made without departing from the scope and spirit of the invention as defined by the attached claims.

What is claimed is:

1. A method for selecting the coloration of a bonding composite adapted for being applied to a discolored tooth to neutralize the discoloration of the tooth, said method comprising selecting one of a plurality of different colorations which most closely matches the discoloration of a tooth to be bonded, superimposing on the selected coloration a plurality of transparent regions each of a coloration corresponding to composite material adapted for being bonded onto a tooth, and selecting one of said transparent regions which when superposed on said selected coloration corresponding to the discolored tooth most closely neutralizes said selected coloration.

2. A method as claimed in claim 1 wherein the superimposing of the transparent regions on the selected coloration is effected by relatively rotating two superimposed discs.

3. A method as claimed in claim 2 wherein the discs are relatively rotated about a common axis of rotation.

* * * * *